(12) United States Patent
Kim et al.

(10) Patent No.: US 7,811,612 B2
(45) Date of Patent: Oct. 12, 2010

(54) HERBAL MIXTURE EXTRACT OF NOTOGINSENG RADIX, REHMANNIAE RADIX PREPARATA AND ACANTHOPANACIS CORTEX AND COMPOSITION COMPRISING THE SAME FOR PREVENTION AND TREATMENT OF ARTHRITIS

(75) Inventors: Jung-Keun Kim, Seongnam-si (KR); Se-Won Kim, Cheonan-si (KR); Hyung-Gun Kim, Seoul (KR); Seon-Yle Ko, Daejeon (KR); Dong-Heon Baek, Seoul (KR); Sunhwa Chang, Chonan-si (KR)

(73) Assignee: Oscotec Inc., Chungcheongnam-Do (KR)

( * ) Notice: Subject to any disclaimer, the term of this patent is extended or adjusted under 35 U.S.C. 154(b) by 201 days.

(21) Appl. No.: 11/781,115

(22) Filed: Jul. 20, 2007

(65) Prior Publication Data
US 2007/0275103 A1    Nov. 29, 2007

Related U.S. Application Data

(63) Continuation of application No. PCT/KR2006/000199, filed on Jan. 18, 2006.

(30) Foreign Application Priority Data
Jan. 20, 2005    (KR)    ............... 10-2005-0005425

(51) Int. Cl.
*A61K 36/25*    (2006.01)
*A61K 36/258*    (2006.01)
*A61K 36/00*    (2006.01)

(52) U.S. Cl. ............................ 424/728; 424/725
(58) Field of Classification Search .............. None
See application file for complete search history.

(56) References Cited

U.S. PATENT DOCUMENTS

2004/0105902 A1 *   6/2004   Chen ................ 424/756

2006/0110468 A1 *   5/2006   Liu et al. ............... 424/725
2007/0154575 A1 *   7/2007   Shimoda et al. ......... 424/756

FOREIGN PATENT DOCUMENTS

| JP | 1994-107556 A | | 4/1994 |
| JP | 11139979 A | * | 5/1999 |
| KR | 2000-0054394 A | | 9/2000 |
| KR | 2001-0106082 A | | 11/2001 |
| KR | 2003034825 A | * | 5/2003 |
| KR | 2004-0079742 A | | 9/2004 |
| KR | 2004079742 A | * | 9/2004 |
| KR | 2004-0100760 A | | 12/2004 |
| WO | WO 03/059370 A1 | | 7/2003 |
| WO | WO 03/094947 A1 | | 11/2003 |
| WO | WO 2005/023281 A1 | | 3/2005 |

OTHER PUBLICATIONS

Hofbauer, L. C., Heufelder, A. E., Arthritis and Rheumatism 44:253-259, 2001.
Firestein, G. S., Nature 423:356-361, 2003.
Udegawe, N., Kotake, S., Kamatani, N., Takahashi, N., and Suda, T., Arthritis Research 4:281-289, 2002.
Kong Y. Y., Feige U., Sarosi I., et al., Nature 402:304-309, 1999.
Linsley, P. and Ledbetter, J. Ann. Rev. Immunol. 11:191-212, 1993.
Schwartz. R. H Cell 71:1065-1068. 1992.
Langenegger, T., Michel, B.A., Clin Orthop. 366:22-30, 1999.
Simon L. S., Int. J. Clin. Pract., 54:243-249, 2000.
Courtenay J. S., Dallman M J., Dayan AD et al., Nature 283 666-668, 1980.

* cited by examiner

*Primary Examiner*—Christopher R. Tate
(74) *Attorney, Agent, or Firm*—Lucas & Mercanti, LLP

(57) ABSTRACT

The present invention relates to an extract of an herbal mixture of *Notoginseng radix*, *Rehmanniae radix preparata* and *Acanthopanacis cortex*, and a method for treating arthritis using the extract as an effective ingredient. The extract of the herbal mixture of the present invention can effectively inhibits the release of inflammatory substances and the synthesis of cartilage destroying substance as well as the progress of arthritis.

15 Claims, 4 Drawing Sheets

□ Hot water extract of Notoginseng radix

▨ Hot water extract of Rehmanniae radix preparata

▨ Hot water extract of Acanthopanacis cortex

■ Hot water mixed extract of Notoginseng radix/ Rehmanniae radix preparata/ Acanthopanacis cortex □ Hot water extract of Notoginseng radix ▨ Hot water extract of Rehmanniae radix preparata ▨ Hot water extract of Acanthopanacis cortex ■ Hot water mixed extract of Notoginseng radix/ Rehmanniae radix preparata/ Acanthopanacis cortex —◇— control
—■— Hot water extract of Notoginseng radix
—✱— Hot water extract of Rehmanniae radix preparata
—○— Hot water extract of Acanthopanacis cortex
—♦— Hot water mixed extract of Notoginseng radix/ Rehmanniae radix preparata/ Acanthopanacis cortex

HERBAL MIXTURE EXTRACT OF NOTOGINSENG RADIX, REHMANNIAE RADIX PREPARATA AND ACANTHOPANACIS CORTEX AND COMPOSITION COMPRISING THE SAME FOR PREVENTION AND TREATMENT OF ARTHRITIS

CROSS-REFERENCE TO RELATED APPLICATIONS

This application is a continuation of PCT International Application No. PCT/KR2006/000199, filed on Jan. 18, 2006, which claims the benefit of priority from Korean Patent Application No. 10-2005-0005425 filed on Jan. 20, 2005.

TECHNICAL FIELD

The present invention relates to a herbal mixture extract of *Notoginseng radix, Rehmanniae radix preparata* and *Acanthopanacis cortex* and a composition for the prevention and the treatment of arthritis comprising the same as an effective ingredient.

BACKGROUND ART

Arthritis related diseases are the representative degenerative intractable diseases, which give 12% of total earth population pain. And over 2 million peoples are suffering from such diseases in Korea.

Arthritis is the general term for symptoms over all the musculoskeletal system caused by inflammatory changes in musculoskeletal and connective tissues. The disease is characterized by chronic inflammation causing permanent damage in tissues, deformity, degeneration and other troubles in joint, bone, cartilage and the spinal cord [Hofbause, L. C., Heufelder, A. E.: The role of osteoprotegerin and receptor activator of nuclear factor kappaB ligand in the pathogenesis and treatment of rheumatoid arthritis, *Arthritis and Rheumatism* 44:253-259, 2001]. Arthritis is classified into degenerative arthritis (osteoarthritis), rheumatoid arthritis, non-joint rheumatism and collagen disease.

Degenerative arthritis, which is the most common of all arthritis related diseases, is developed by local degeneration by the worn-out of joint cartilage. The cause of the disease is still unclear but aging or over-weight might be the reason. Primarily, degenerative changes appear in joint cartilage. Degeneration first begins in joint cartilage and chondrocytes are killed and then cartilage matrix is destroyed by cathepsin B, cathepsin D, collagenase, etc. The destruction outpaces the generation of proteoglycan and collagen, and adaptability of cartilage to outside force becomes weaker, resulting in microfractures in subchondral bone tissues. As the disease progresses, the hardening of subchondral bone, over-ossification around joint, joint deformation, etc. are observed. Then, the surface of cartilage becomes rough and inflammation in joint cavity enveloped by joint capsule repeats, resulting in constant pain, ankylosis and gradual motor disturbance in joint.

One kind of arthritis, rheumatoid arthritis is a chronic inflammatory disease over the whole body and its symptoms occur symmetrically to movable joints. The disease is also known as an autoimmune disease caused by malfunction of immune system. However, the cause of the disease is still in question. Rheumatoid arthritis is characterized by continuous inflammatory synovitis causing the destruction of cartilage and bone erosion, resulting in deformity of joint structure. Symptoms of rheumatoid arthritis are joint edema, joint tenderness, inflammation. Symptoms of osteoarthritis are morning stiffness and acute pain with bending of a joint. As the disease progresses, structural damage can be found such as bone erosion and joint destruction [Firestein, G. S.: Evolving concept of rheumatoid arthritis, *Nature* 423:356-361, 2003]. In addition, a patient with rheumatoid arthritis might suffer from other symptoms by additional organ damage, for example damage of skin, kidney, heart, lung, central nervous system and eye, which is resulted from vasculitis related to autoimmune process. Arthritis related other symptoms include acceleration of erythrocyte sedimentation rate and increase of the concentration of serum C-reactive protein (CRP) or soluble IL-2 receptor (IL-2r). The acceleration of erythrocyte sedimentation rate is detected in almost every active rheumatoid arthritis patients. The concentration of serum C-reactive protein also increases in those patients. It is related to the activation of the disease and the possibility of progressive joint damage. The concentration of soluble IL-2r, a product of T-cell activation, increases in serum and synovial fluid of active rheumatoid arthritis patients, too [Udagawa, N., Kotake, S., Kamatani, N., Takahashi, N., and Suda, T: The molecular mechanism of osteoclastogenesis in rheumatoid arthritis. Arthritis Research 4:281-289, 2002].

It is generally believed that Th1 type CD4+ T cells play an important role in the progress and continuation of rheumatoid arthritis. That is, CD4+ T lymphocytes stimulate macrophages and synovial cells to have inflammatory cytokines (TNF-α, IFN-γ, GM-CSF, IL-2, IL-6) and matrix metalloproteinase (MMP) secreted, for which signals were transmitted by soluble materials such as interferon-gamma (IFN-γ) and IL-17 and by cell surface component such as CD69. The secreted cytokines stimulate the proliferation of synovial membrane to form a pannus and destroy cartilage in cooperation with matrix metalloproteinase. The activated CD4+ T cells induce the activation of B cells through the contact with them on cell surface by CD40L, CD28, and a1b2 integrin, leading to the production of antibody containing rheumatoid factors. When CD4+ T cells are activated, osteoprotegerin ligand (OPGL) is expressed on the surface, which stimulates osteoclastogenesis, an important factor for bone destruction [Kong Y. Y., Feige U., Sarosi I., et al.: Activated T cells regulate bone loss and joint destruction in adjuvant arthritis through osteprotegerin ligand. *Nature* 402:304-309, 1999]. The activated macrophages and fibroblasts accelerate angiogenesis by secreting VEGF, FGF, etc. The activated vascular endothelial cells in synovial membrane make an amplified cycle of inflammation by secreting chemokine such as IL-8, inducing the expression of adhesion molecule and speeding up the infiltration of inflammatory cells. Rheumatoid arthritis is also believed to be a T-cell mediated autoimmune disease, which is related to the non antigen-specific intracellular interaction between T-lymphocytes and antigen-presenting cells. The reaction size of T-cells is determined by simultaneous stimuli induced by the interaction between a T-cell surface molecule and its' ligand. A major simultaneous stimulus signal is given by the interaction between T-cell surface receptors, CD28 and CTLA4, and their ligands such as B7-related molecules on antigen-presenting cells, that is CD80 (B7-1) and CD86 (B7-2) [Linsley, P. and Ledbetter, J.: The role of the CD28 receptor during T cell responses to antigen. *Ann. Rev. Immunol.* 11:191-212, 1993]. T-cell activation without simultaneous stimuli results in anergic T-cell response, indicating that immune system does not response to a stimulus [Schwartz, R. H.: Costimulation of T lymphocytes: the role of CD28, CTLA-4, and B7/BB1 in interleukin-2 production and immunotherapy. *Cell* 71:1065-1068, 1992].

The treatment method for degenerative arthritis and rheumatoid arthritis in use is as follows. For the primary care, non-steroidal anti-inflammatory drug (NSAID) has been used, which improves patient's conditions but cannot prevent the progress of the disease and the damage of joint cartilage. In addition, such medicine is supposed to be administered for a long time, but long-term administration of the drug causes side effects in gastrointestinal system, central nervous system, hematopoietic tissues, kidney, liver, etc. So, half of the patients being treated with NSAID should give up the treatment within a year [Langenegger, T., Michel, B. A.: Drug treatment for rheumatoid arthritis., *Clin Orthop.* 366:22-30, 1999]. For the next treatment step, disease modifying antirheumatic drugs (DMARDs) such as gold drugs which are gold containing compounds like gold sodium thiomalate, gold sodium thiosulfate, etc, penicillamine and anti-malarials, have been used. Although these drugs reduce the progress of arthritis to some degree, they carry serious side-effects, too. Thus, only 5~15% patients keep being treated with these drugs continuously after 5 years from the first administration of DMARDs. If no more therapeutic effects are expected from those drugs, the arthritic developed joint has to be replaced with artificial joint by surgical operation [Simon L. S., *Int. J. Clin. Pract.*, 54:243-249, 2000].

Therefore, it is an urgent need to develop a new substance effective for the prevention and the treatment of arthritis related diseases, which has a new structure and functions to minimize side effects and toxicity, the limitations of the conventional therapeutic agents.

Thus, the present inventors have studied various physiological activities of *Notoginseng radix, Rehmanniae radix preparata* and *Acanthopanacis cortex*, and as a result the present inventors completed this invention by confirming that herbal mixture extract of *Notoginseng radix, Rehmanniae radix preparata* and *Acanthopanacis cortex* has no toxicity, inhibits the release of an inflammatory substance and the synthesis of a matrix destroying factor and suppresses the progress of arthritis, making it as a promising candidate without side effects for preventive and therapeutic agent as well as health food for arthritis related diseases.

DISCLOSURE

Technical Problem

It is an object of the present invention to provide a herbal mixture extract of *Notoginseng radix, Rehmanniae radix preparata* and *Acanthopanacis cortex* having activities of inhibiting the release of an inflammatory substance and the synthesis of a matrix destroying factor.

It is another object of the present invention to provide a composition for the prevention and the treatment of arthritis containing the above extract as an effective ingredient.

Technical Solution

To achieve the above object, the present invention provides a herbal mixture extract of *Notoginseng radix, Rehmanniae radix preparata* and *Acanthopanacis cortex* having activities of inhibiting the release of an inflammatory substance and the synthesis of a matrix destroying factor.

The present invention also provides a composition for the prevention and the treatment of arthritis containing the above extract as an effective ingredient.

ADVANTAGEOUS EFFECTS

The herbal mixture extract of *Notoginseng radix, Rehmanniae radix preparata* and *Acanthopanacis cortex* of the present invention has excellent activities of inhibiting the release of an inflammatory substance, which is one of the critic causes of arthritis, and suppressing the synthesis of a matrix destroying substance (MMP-13), which is a cartilage destroying factor, compared with an individual extract of each. Moreover, inhibition of the progress of arthritis in animal models was greater when the herbal mixture extract of the present invention was administered than when single extract of each was administered respectively. Therefore, the herbal mixture extract of *Notoginseng radix, Rehmanniae radix preparata* and *Acanthopanacis cortex* can be effectively used not only for the prevention and the treatment of arthritis but also for improving health condition.

DESCRIPTION OF DRAWINGS

The application of the preferred embodiments of the present invention is best understood with reference to the accompanying drawings, wherein.

BEST MODE

Figure 1:
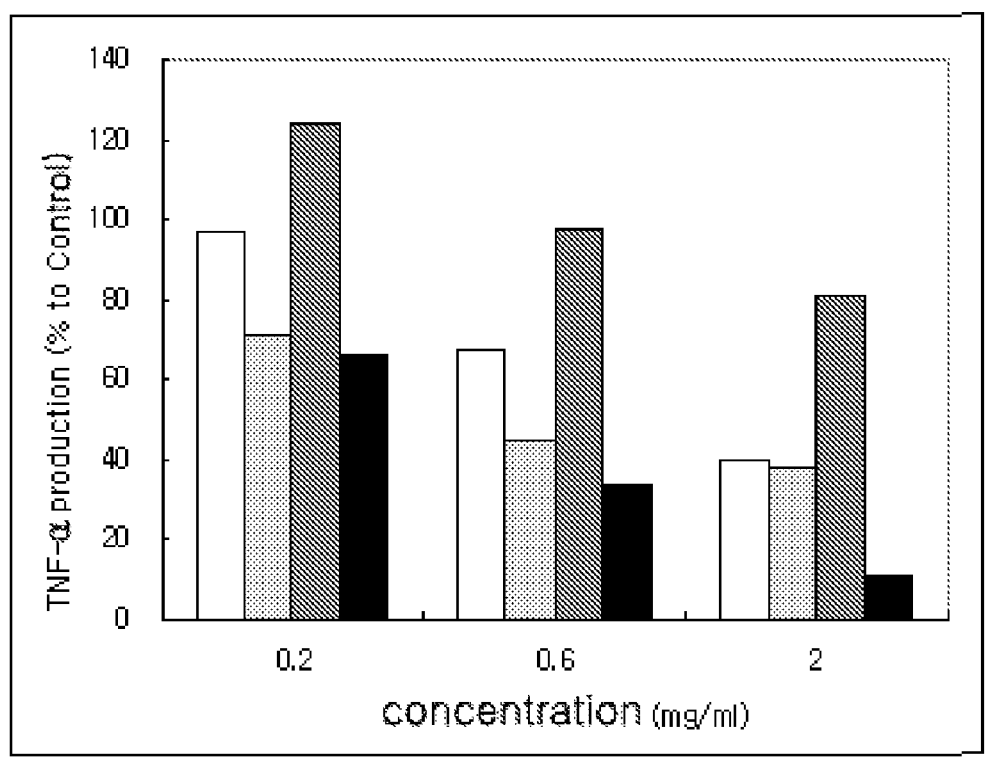
FIG. 1 is a graph showing the inhibitory effect of the herbal mixture extract of the present invention on the release of TNF-$\alpha$, an inflammatory substance.

Hereinafter, the present invention is described in detail.

*Notoginseng radix* (*Panax notoginseng* (Burk.) F. H. Chen) is a root of a perennial herb belonging to Araliaceae. It is smaller than a ginseng and has 7 pieces of leaves. Its' root is in a small thread drum shape and it is raised widely in Yunnan and Sichuan, southern China. Since the plant has 7 leaves on three branches, it has been called 'Samchil (three-seven)' and often called 'Samchil ginseng' owing to its similar appearance to Korean ginseng. The root has 3~8% saponin and its' major components are ginsenoside $Rb_1$, $Rg_1$, and Re, and notoginsenoside $R_1$, $R_2$, Fa and Fc but small amount of ginsenoside $R_2$, $b_2$, d, e, c are also included. $R_0$ is not contained or if it is, it must be least. Essential oil composition is fewer in *Notoginseng radix* than in *Panax ginseng*. *Notoginseng radix* additionally includes oleanolie acid. Its' root has hemostatic and cardiotonic activities. It was confirmed from animal tests that the root has efficacy of increasing blood flow of coronary artery, decreasing oxygen consumption and lowering the levels of lipid and cholesterol in blood. *Notoginseng radix* also has functions of anti-inflammation, analgesia and hemostasis, so that it is very useful for the treatment of not only inflammatory diseases including hepatitis but also bleeding from trauma, cut, etc, and internal hemorrhage. Applying to a wound or oral administration give the same effects.

*Rehmanniae radix preparata* is a root of a medicinal plant belonging to Scrophulariaceae, which has been used as a traditional oriental medicine after being steamed and dried. The raw *Rehmanniae radix preparata* is called *Rehmanniae radix crudus* Libosch, and the dried *Rehmanniae radix preparata* is called *Rehmanniae radix* Libosch. In particular, the one which has been through steam-dry processes after being dipped in alcohol drink nine times is called 'Gujiwhang', whose medicinal effect is known as the best. It has sweet and bitter taste at the same time and has property of making things warm, by which it can supplement blood and energy (a basic substance necessary for the life and vital activity) so that it helps the treatment of the coldness of knees and lower back and menstrual irregularity, in addition to making hair black and healthy. *Rehmanniae radix preparata* is one of major components for Samultang and has been administered for relieving fever, dried throat and dipsesis, symptoms of being weak. Besides, it has been known in folk remedies that *Rehmanniae radix preparata* shows therapeutic effect on constipation when it is administered together with pork soup.

*Acanthopanacis cortex* is a shrub belonging to Araliaceae, which is only found in far-east Asia in northern hemisphere. In particular, *Acanthopanacis cortex* is classified as a reserved wild plant in South Korea, which is on the brink of extinction. *Acanthopanacis cortex* is divided into *Acanthopanax senticosus, Acanthopanax* and *Acanthopanax koreanum*. The roots and barks of *Acanthopanacis cortex* have been used as top-ranked medicine since they have not shown any toxicity or side effects so far. The leaf of *Acanthopanacis cortex* contains chiisanoside, which has pharmacological effect. The roots of *Acanthopanacis cortex* contains not only *Acanthopanacis cortex* glycoside but also syringin and coumarin glycosides. *Acanthopanacis cortex* contains acanthosides B and D, which are *Acanthopanacis cortex* glycosides, and water-soluble polysaccharides enhancing immunity. Its' taste is bitter and hot and it has a property of warming things up. It is known to eliminate gout in liver and nervous systems, invigorate and bring essence in a body. It has been prescribed for such diseases as Oro (fatigue caused by the weakness of five internal organs), Chilsang (seven representative symptoms shown in men caused by the weakness of a body) and difficulty in moving legs. Long-term administration of *Acanthopanacis cortex* increases energy, protects the stomach, invigorates, clears mind, increases will power, prevents aging, helps having a light heart and clear the blood in a body. So, *Acanthopanacis cortex* has been used for the treatment of such symptoms as pain in backbone, male impotence, scrotal eczema, female amenorrhea, etc.

The herbal mixture extract of *Notoginseng radix, Rehmanniae radix preparata* and *Acanthopanacis cortex* of the present invention is extracted by using water, $C_1$~$C_4$ alcohol or a mixture of the two, and the extraction processes are as follows.

*Notoginseng radix, Rehmanniae radix preparata* and *Acanthopanacis cortex* are washed with water and dried in the shadow. They are put in an extraction vessel, to which distilled water is added, followed by hot water extraction. The mixture is cooled down at room temperature, followed by filtering with a filter paper. Then, the extract is concentrated under the reduced pressure by using vacuum rotation evaporator, followed by freeze-drying, resulting in herbal mixture powder extract. More precisely, the herbal mixture is composed of 30~70 weight part of *Notoginseng radix,* 20~60 weight part of *Rehmanniae radix preparata* and 0.5~20 weight part of *Acanthopanacis cortex*, more preferably 40~60 weight part of *Notoginseng radix,* 30~50 weight part of *Rehmanniae radix preparata* and 5~15 weight part of *Acanthopanacis cortex*, and most preferably 50 weight part of *Notoginseng radix,* 40 weight part of *Rehmanniae radix preparata* and 10 weight part of *Acanthopanacis cortex*.

Compared with individual extracts of each *Notoginseng radix, Rehmanniae radix preparata* and *Acanthopanacis cortex*, the herbal mixture extract of the three of the present invention has 2~8 times as excellent inhibitory effect on the release of inflammatory substances such as TNF-α and nitric oxide (NO) as each individual extract. In addition, the mixture extract of the invention drastically inhibits the synthesis of matrix destroying substance, for example a destroyer of cartilage, or matrix metalloproteinas-13, compared with when a single extract is treated at the same concentration.

The herbal mixture extract of the present invention also inhibits remarkably the progress of arthritis, compared with when a single extract of each *Notoginseng radix, Rehmanniae radix preparata* and *Acanthopanacis cortex* is treated.

Accordingly, the herbal mixture extract of the present invention has excellent activities of inhibiting the synthesis of an inflammatory substance such as TNF-α or nitric oxide, and suppressing the progress of arthritis in animal models, suggesting that it can be effectively used for the prevention and the treatment of arthritis.

The herbal mixture of the present invention was orally administered to mice to investigate toxicity. As a result, it was evaluated to be safe substance since its estimated $LD_{50}$ value (50% lethal dose) is much greater than 5,000 mg/kg in mice.

The present invention also provides a composition for the prevention and the treatment of arthritis containing the above extract as an effective ingredient.

The composition of the present invention can additionally include, in addition to the herbal mixture extract, one or more effective ingredients having the same or similar functions to the extract of the invention.

The herbal mixture extract of the present invention can be administered orally or parenterally and be used in general forms of pharmaceutical formulation.

The herbal mixture extract of the present invention can be prepared for oral or parenteral administration by mixing with generally used fillers, extenders, binders, wetting agents, disintegrating agents, diluents such as surfactant, or excipients. Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used. Liquid formulations for oral administrations are suspensions, solutions, emulsions and syrups, and the abovementioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc. In addition, calcium or vitamin D3 can be included to enhance the preparative or therapeutic effect on arthritis.

The effective dosage of the composition can be determined according to weight, age, gender, health condition, diet, administration frequency, administration method, excretion and severity of a disease. The dosage of the composition is 0.1~100 mg/kg per day, and preferably 30~86 mg/kg per day. More preferably, the dosage is 50~60 mg/kg per day. Administration frequency is 1~6 times a day.

The composition of the present invention can be administered singly or treated along with surgical operation, hormone therapy, chemotherapy and biological reaction regulator, to prevent and treat arthritis.

The composition of the present invention can be included in health food for the purpose of improving arthritis. At this time, the herbal mixture extract of the present invention can be added as it is or after being mixed with other food or ingredients, according to the conventional method. The mixing ratio of effective ingredients is determined by the purpose of use (prevention, health or therapeutic treatment). However, the content of the extract might be less than the above when it is administered for long-term to improve health conditions but the effective dosage could contain more than the above amount because the extract of the invention is very safe.

There is no limit in applicable food, which is exemplified by meats, sausages, bread, chocolate, candies, snacks, cookies, pizza, ramyun, noodles, dairy products including ice cream, soups, beverages, tea, drinks, alcoholic drinks and vitamin complex, etc, and in fact every health food generally produced are all included.

Health beverages containing the composition of the present invention can additionally include various flavors or natural carbohydrates, etc, like other beverages. The natural carbohydrates above can be one of monosaccharide such as glucose and fructose, disaccharides such as maltose and sucrose, polysaccharides such as dextrin and cyclodextrin, and sugar alcohols such as xilytole, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01~0.04 g to 100 ml, more preferably 0.02~0.03 g to 100 ml.

In addition to the ingredients mentioned above, the composition of the present invention can include in variety of nutrients, vitamines, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01~0.1 weight part per 100 weight part of the composition of the invention.

MODE FOR INVENTION

Practical and presently preferred embodiments of the present invention are illustrative as shown in the following Examples. However, it will be appreciated that those skilled in the art, on consideration of this disclosure, may make modifications and improvements within the spirit and scope of the present invention.

EXAMPLE 1

Preparation of Herbal Extracts

Cultivated *Notoginseng radix*, *Rehmanniae radix preparata* and *Acanthopanacis cortex* were purchased from a wholesale dried medicinal herb store.

<1-1> Preparation of *Notoginseng radix* Extract

*Notoginseng radix* was washed with clean water and dried in the shadow. 100 g of the dried *Notoginseng radix* was put in a 3 l extraction vessel, to which 1 l of distilled water was added, followed by hot water extraction for 4 hours at 100° C. The process was repeated three times, and the resultant solution was cooled down at room temperature, followed by filtering with a filter paper. The extracted solution was concentrated under reduced pressure under 40° C. by using vacuum rotary evaporator, followed by freeze-drying. As a result, powder extract of *Notoginseng radix* was obtained (yield: 15%).

<1-2> Preparation of *Rehmanniae radix preparata* Extract

*Rehmanniae radix preparata* was washed with clean water and dried in the shadow. 100 g of the dried *Rehmanniae radix preparata* was put in a 3 l extraction vessel, to which 1 l of distilled water was added, followed by hot water extraction for 4 hours at 100° C. The process was repeated three times, and the resultant solution was cooled down at room temperature, followed by filtering with a filter paper. The extracted solution was concentrated under reduced pressure under 40° C. by using vacuum rotary evaporator. As a result, *Rehmanniae radix preparata* extract was obtained (yield: 42%).

<1-3> Preparation of *Acanthopanacis cortex* Extract

*Acanthopanacis cortex* was washed with clean water and dried in the shadow. 100 g of the dried *Acanthopanacis cortex* was put in a 3 l extraction vessel, to which 1 l of distilled water was added, followed by hot water extraction for 4 hours at 100° C. The process was repeated three times, and the resultant solution was cooled down at room temperature, followed by filtering with a filter paper. The extracted solution was concentrated under reduced pressure under 40° C. by using vacuum rotary evaporator, followed by freeze-drying. As a result, powder extract of *Acanthopanacis cortex* was obtained (yield: 10%).

<1-4> Preparation of Herbal Mixture Extract of *Notoginseng radix/Rehmanniae radix preparata/Acanthopanacis cortex*

Each herb was washed with clean water, and dried in the shadow. 50 g of *Notoginseng radix* was pulverized, so were *Rehmanniae radix preparata* (40 g) and *Acanthopanacis cortex* (10 g). The herbs were put in a 3 l extraction vessel, to which 20 times as much as water was added, followed by hot water extraction for 8 hours at 95° C. The heated extract was cooled down at room temperature and filtered. The resultant solution was concentrated under reduced pressure under 40° C. by using vacuum rotary evaporator, followed by freeze-drying. As a result, 28.7 g of powder herbal mixture extract was obtained. The powder extract was dissolved in 120 ml of distilled water to be used for the following experiments.

EXPERIMENTAL EXAMPLE 1

Inhibitory Effect of the Herbal Mixture Extract on the Release of TNF-α

Following experiments were performed to investigate the inhibitory effect on TNF-α, a cytokine released from THP-1 cells which are human monocytic cell line, of the herbal mixture extract of the present invention.

<1-1> Selection and Culture of Cells

To evaluate the effect of the herbal mixture extract of the invention on the release of TNF-α, a human originated cell line THP-1 (ATCC No. TIB-202) was distributed from ATCC (USA). The cells were cultured in RPMI 1640 (Gibco, BRL, USA) medium supplemented with 10% FBS (fetal bovine serum) and 0.05 mM 2-mercaptoethanol, in a 37° C. $CO_2$ incubator.

<1-2> Quantification of Released TNF-α

In order to investigate the effect of the herbal mixture extract of the present invention on the release of TNF-α, the amount of released TNF-α was measured by ELISA using cells prepared in the Experimental Example <1-1>. Particularly, the cells were distributed into a 96-well plate by $5 \times 10^5$ cells/well and lipopolysaccharide (LPS) was added in order to activate cells for the release of TNF-α. An experimental group was treated with the herbal mixture extract prepared above at different concentrations for 24 hours together with LPS. After the treatment, the released TNF-α in culture broth was quantified by ELISA. $OD_{450}$ was measured by using Dynatech MR-7000 (Dynatech Laboratorie Co.). The amount of released TNF-α was calculated as a percentage for that of a control (treated with LPS only). The inhibitory effect on the release of TNF-α according to the concentrations of herbal mixture extract is shown in FIG. 1.

As shown in FIG. 1, the released TNF-α in cells treated with the herbal mixture extract of the present invention by the concentration of 2 mg/ml was 10.6%, which was 4~8 fold higher inhibitory effect on the release of TNF-α, compared with cells treated with each extract of *Notoginseng radix, Rehmanniae radix preparata* and *Acanthopanacis cortex* (39.9%, 38.1% and 80.9%, respectively).

EXPERIMENTAL EXAMPLE 2

Inhibitory Effect of the Herbal Mixture Extract on NO Generation

Following experiments were performed to investigate the inhibitory effect of the herbal mixture extract of the invention on NO (an inflammation mediator) generation in RAW264.7, a mouse macrophage cell line.

<2-1> Selection and Culture of Cells

To evaluate the effect of the herbal mixture extract of the invention on the generation of nitric oxide, a mouse originated cell line RAW264.7 (ATCC No. TIB-71) was distributed from ATCC (USA). The cells were cultured in DMEM (Gibco, BRL, USA) supplemented with 10% FBS (fetal bovine serum), in a 37° C. $CO_2$ incubator.

<2-2> Quantification of NO Generation

To investigate the effect of the herbal mixture extract of the present invention on NO generation, the amount of NO generated in cells prepared in the Experimental Example <2-1> was measured. Particularly, the cells were distributed into a 96-well plate by $5 \times 10^5$ cells/well and lipopolysaccharide (LPS) was added in order to activate cells for the release of NO. An experimental group was treated with the herbal mixture extract prepared in the Example 1 at different concentrations for 12 hours together with LPS. After the treatment, the generated NO in culture broth was quantified by Griess reaction.

Figure 2:
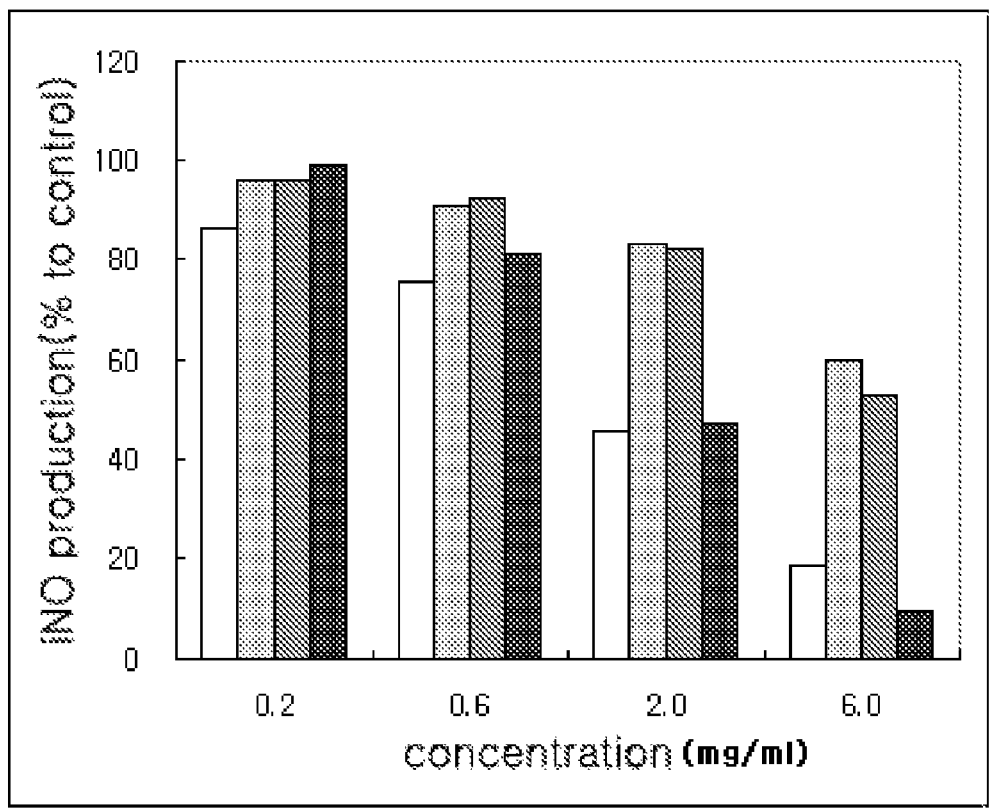
FIG. 2 is a graph showing the inhibitory effect of the herbal mixture extract of the present invention on the release of nitric oxide (NO), another inflammatory substance.

The quantification of NO generation according to the concentration of herbal mixture extract of the invention is shown in FIG. 2.

As shown in FIG. 2, the NO generation was greatly inhibited in cells treated with the herbal mixture extract of the present invention, compared with in cells treated with each extracts of *Notoginseng radix, Rehmanniae radix preparata*, and *Acanthopanacis cortex*, respectively. In particular, the inhibitory effect on NO generation at the herbal mixture extract concentration of 6 mg/ml was approximately 2~6 times higher than that of each individual extract.

EXPERIMENTAL EXAMPLE 3

Inhibitory Effect of the Herbal Mixture Extract on the Synthesis of MMP

Following experiments were performed to investigate the effect of the herbal mixture extract on the synthesis of matrix metalloproteinase-13 (MMP-13), a matrix destroying factor, produced in human chondrosarcoma cell line SW1353.

<3-1> Selection and Culture of Cells

To evaluate the effect of the herbal mixture extract of the invention on the synthesis of MMP-13, a human originated cell line SW1353 (ATCC No. HTB-94) was distributed from ATCC (USA). The cells were cultured in DMEM (Gibco, BRL, USA) supplemented with 10% FBS (fetal bovine serum), in a 37° C. $CO_2$ incubator.

<3-2> Quantification of the Synthesis of MMP-13

To investigate the effect of the herbal mixture extract of the present invention on the synthesis of MMP-13, the expression of MMP-13 in the cells prepared in the Experimental Example <3-1> was measured. Particularly, the cells were distributed into a 96-well plate by $5 \times 10^5$ cells/well. 24 hours later, the cells were washed with PBS (NaCl 8 g, KCl 0.2 g, $Na_2HPO_4$ 1.44 g, $KH_2PO_4$ 0.24 g/1 l distilled water, pH 7.4) and cultured in FBS-free DMEM for 24 hours again. An experimental group was treated with the herbal mixture extract prepared in the Example 1 for one hour. Then, both experimental and control groups were treated with TNF-α. 24 hours later, the amounts of MMP-13 in both cell culture solutions were measured by Western blotting. That is, the cell culture solution was placed on SDS-polyamide gel, followed by electrophoresis, and then the gel was transferred onto a membrane by using half-dried blotter (TRANS-BLOT SD system, Biorad). The membrane was washed with TBS-T (10 mM Tris-buffered saline, 0.1% Tween-20, pH 7.2), which was left in blocking solution (3% skim milk) for one hour. One hour later, the membrane was washed twice with TBS-T, which was reacted with 1:3,000~5,000 diluted monoclonal antibody (Chemicon) against human MMP-13 for 2 hours. Upon completion of the reaction, the membrane was washed with TBS-T three times, and reacted with diluted horseradish peroxidase-conjugated goat anti-mouse IgG (Promega) for one hour. After then, the membrane was washed again 3~4 times, followed by confirmation with ECL (enhanced chemiluminesence) Western blot analysis system (Amersham).

Figure 3:
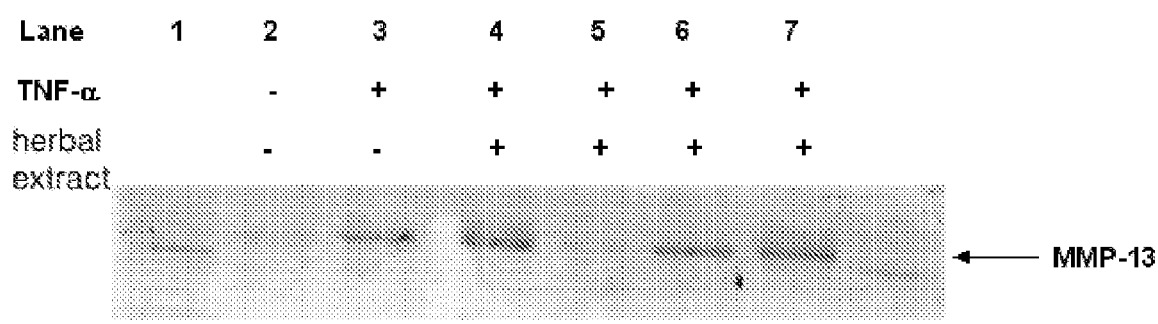
FIG. 3 is a photograph showing the inhibitory effect of the herbal mixture extract of the present invention on the synthesis of matrix metalloproteinase (MMP-13), a cartilage matrix destroying substance.

The effect of the herbal mixture extract of the invention on the expression of MMP-13 is shown in FIG. 3.

As shown in FIG. 3, individual extracts of each *Notoginseng radix, Rehmanniae radix preparata* and *Acanthopanacis cortex* and the herbal mixture extract of the three of the present invention were treated to cells by the same concentration (6 mg/ml per each). As a result, when the herbal mixture extract was treated, the band was remarkably reduced, compared with when each extract was treated singly, indicating that the herbal mixture extract of the present invention has excellent inhibitory effect on the synthesis of MMP-13.

EXPERIMENTAL EXAMPLE 4

Acute Toxicity Test with the Herbal Mixture Extract of the Present Invention

The herbal mixture extract of the present invention is safe since the medicinal herbs used in the invention classified into a food material. But, for the use as a treatment medicine, acute toxicity of the extract had to be investigated as follows. 6-week old SPF mice were used in the tests for acute toxicity. The herbal mixture extract of the present invention was suspended in 0.9% NaCl and orally administered once to 10 mice per group at the dosage of 2 and 5 g/kg. Death, clinical symptoms, and weight change in mice were observed, hematological tests and biochemical tests of blood were performed, and any abnormal signs in the gastrointestinal organs of chest and abdomen were checked with eyes during autopsy.

The results showed that the herbal mixture extract of the present invention did not cause any specific clinical symptoms, weight change, or death in rats. No change was observed in hematological tests, biochemical tests of blood, and autopsy. Therefore, the herbal mixture extract used in this experiment was evaluated to be safe substances since it did not cause any toxic change in mice up to the level of 5 g/kg and its estimated $LD_{50}$ values are much greater than 5 g/kg in mice.

EXPERIMENTAL EXAMPLE 5

Inhibition of the Progress of Arthritis in Test Animals with Type 2 Collagen Induced Arthritis by the Herbal Mixture Extract of the Present Invention In order to investigate whether or not the herbal mixture extract of the present invention could inhibit the progress of arthritis in test animals having type 2 collagen induced arthritis, following experiments were performed.

<5-1> Inducement of Arthritis in Test Animals

To prepare test animals having type 2 collagen induced arthritis, 5~6 week old male DBA1 mice were purchased from SCI Co., Japan, and the mice were raised at 21° C. with 40% humidity. Bovine type 2 collagen (Condrex Co., Japan) was dissolved in 0.05% acetic acid, making the concentration 2 mg/ml. Then the type 2 collagen was mixed with the same amount of complete adjuvant (Condrex Co., Japan). While cooling down with ice, the mixture became homogeneous suspension by using T-connector linked to 3 ml syringe. After confirming the suspension was prepared rightly, tail head of a mouse was sterilized with alcohol cotton and 100 μl of collagen suspension was injected under the skin of the tail head.

<5-2> Oral Administration of the Herbal Mixture Extract of the Present Invention The herbal mixture extract of the present invention prepared in the Example 1 was dissolved in water, followed by filtering with 0.25 μM filter. The filtered solution was administered to the mouth of a mouse through sonde linked to a 1 ml syringe, once a day and by 276 mg/kg/day for 3 weeks.

<5-3> Progress of Arthritis: Naked Eye Observation and Diagnosis

It has been known that arthritis is developed approximately 30 days after the first injection of collagen suspension. Naked eye observation on lesion of arthritis was performed by using following scores based on literature cited. 0: No swelling or flair, 1: Light swelling and flair in joint, 2: Clear swelling and flair in joint, 3: Severe swelling and flair in joint including knuckle joint, 4: Severe swelling in all over the joint. Therefore, the highest score of lesion of arthritis is 16 per mouse, which sums up scores of fore legs and hind legs, and the highest score per one leg is 4 [Courtenay J. S., Dallman M. J., Dayan A D, et al.: Immunization against heterologous type II collagen induces arthritis in mice. *Nature* 283:666-668. 1980].

Figure 4:
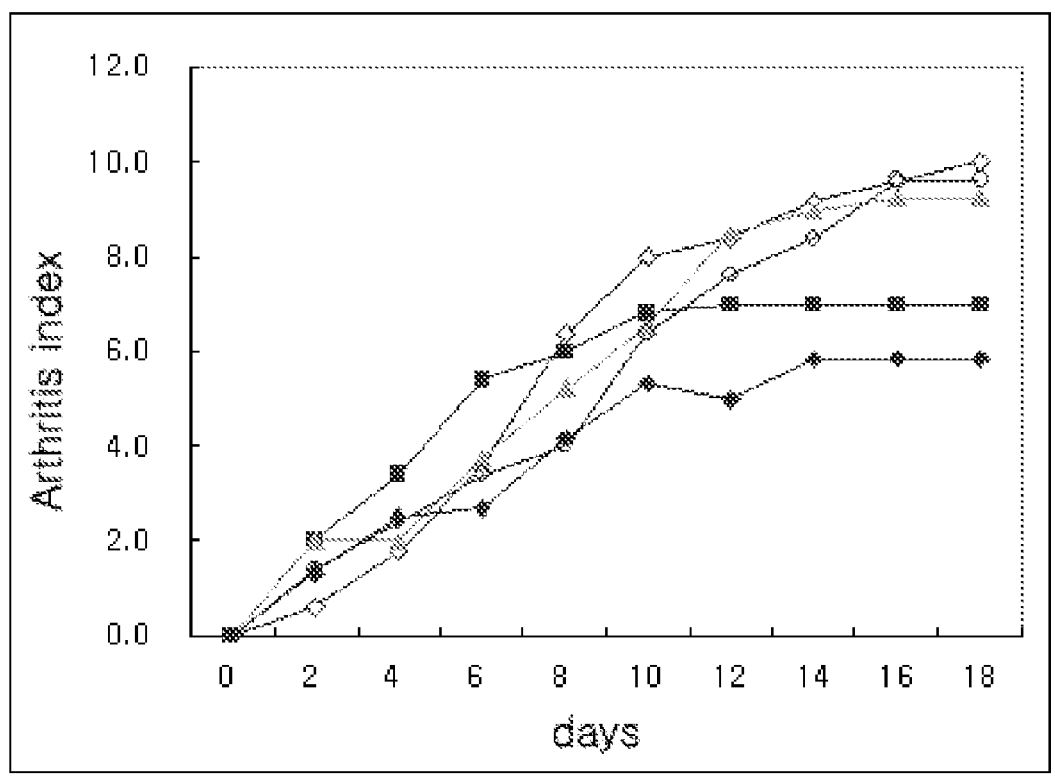
FIG. 4 is a graph showing the inhibitory effect of the herbal mixture extract of the present invention on the progress of arthritis in type 2 collagen induced arthritis animal models.

<5-4> Inhibition of the Progress of Arthritis in Test Animals with Type 2 Collagen Induced Arthritis by the Herbal Mixture Extract of the Present Invention The herbal mixture extract of the present invention was orally administered to test animals with type 2 collagen induced arthritis. And the inhibitory effect on the progress of arthritis thereby is shown in FIG. 4 and in Table 1. As illustrated in FIG. 4 and Table 1, the inhibitory effect on the progress of arthritis of the herbal mixture extract of the invention is greater than that of each individual extracts of *Notoginseng radix, Rehmanniae radix preparata* and *Acanthopanacis cortex*.

TABLE 1

| | | Extract | | | |
|---|---|---|---|---|---|
| Day | Control | Hot water extract of Notoginseng radix | Hot water extract of Rehmanniae radix preparata | Hot water extract of Acanthopanacis cortex | Hot water mixed extract of Notoginseng radix/Rehmanniae radix preparata/Acanthopanacis cortex |
| 0 | 0.0 ± 0.0 | 0.0 ± 0.0 | 0.0 ± 0.0 | 0.0 ± 0.0 | 0.0 ± 0.0 |
| 2 | 0.6 ± 0.5 | 2.0 ± 0.6 | 2.0 ± 0.7 | 1.4 ± 0.8 | 1.3 ± 0.7 |
| 4 | 1.8 ± 0.5 | 3.4 ± 0.7 | 2.0 ± 0.9 | 2.4 ± 0.9 | 2.5 ± 0.8 |
| 6 | 3.6 ± 1.1 | 5.4 ± 1.1 | 3.8 ± 1.2 | 3.4 ± 0.9 | 2.7 ± 0.7 |
| 8 | 6.4 ± 1.6 | 6.0 ± 1.3 | 5.3 ± 1.6 | 4.0 ± 1.1 | 4.2 ± 0.7 |
| 10 | 8.0 ± 1.9 | 6.8 ± 1.4 | 6.5 ± 1.9 | 6.4 ± 1.3 | 5.3 ± 1.2 |
| 12 | 8.4 ± 1.7 | 7.0 ± 1.3 | 8.5 ± 1.4 | 7.6 ± 1.4 | 5.0 ± 1.0 |
| 14 | 9.2 ± 1.8 | 7.0 ± 1.3 | 9.0 ± 1.6 | 8.4 ± 1.5 | 5.8 ± 1.3 |
| 16 | 9.6 ± 1.4 | 7.0 ± 1.3 | 9.3 ± 1.7 | 9.6 ± 1.4 | 5.8 ± 1.3 |
| 18 | 10.0 ± 1.7 | 7.0 ± 1.3 | 9.3 ± 1.7 | 9.6 ± 1.4 | 5.8 ± 1.3 |

The Formulation Examples of the composition for the present invention are described hereinafter.

FORMULATION EXAMPLE 1

Preparation of Pharmaceutical Formulations

<1-1> Preparation of powders

| | |
|---|---|
| Herbal mixture extract | 2 g |
| Lactose | 1 g |

Powders were prepared by mixing all the above components and filled airtight bag with them.

<1-2> preparation of tablets

| | |
|---|---|
| Herbal mixture extract | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of capsules

| | |
|---|---|
| Herbal mixture extract | 100 mg |
| Corn starch | 100 mg |
| Lactose | 100 mg |
| Magnesium stearate | 2 mg |

Capsules were prepared by mixing the components above and filled gelatin capsules with them according to the conventional method for capsules.

FORMULATION EXAMPLE 2

Preparation of Foods

Foodstuff containing the herbal mixture extract of the present invention was prepared as follows.

*153<2-1> Preparation of Flour Foods

Health improving flour food was prepared by adding the herbal mixture extract of the present invention by 0.5~5.0 weight % to wheat flour and then making the flour into bread, cakes, cookies, crackers and noodles.

<2-2> Preparation of Dairy Products

The herbal mixture extract of the present invention was added by 5~10 weight % to milk to prepare health improving dairy products such as butter, ice cream, etc.

<2-3> Preparation of Mixed Sereal Foods

Brown rice, barley, glutinous rice and coix (job's tear) were gelatinizated by the conventional method, followed by drying. The dried mixture was distributed and pulverized, resulting in 60-mesh size grain powders.

Black bean, black sesame and perilla were steamed and dried by the conventional method. The dried mixture was distributed and pulverized, resulting in 60-mesh size grain powders.

The herbal mixture extract of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and dried herbal mixture extract powders were all mixed at the following ratio.

Grain (brown rice 30 weight %, coix 15 weight %, barley 20 weight %),

Seeds (perilla 7 weight %, black bean 8 weight %, black sesame 7 weight %),

Dried powder of herbal mixture extract (3 weight %),

*Ganoderma lucidum* (0.5 weight %),

*Rehmannia glutinosa* (0.5 weight %)

FORMULATION EXAMPLE 3

Preparation of Beverages

<3-1> Preparation of Carbonated Beverages

Sugar (5~10%), citric acid (0.05~0.3%), caramel (0.005~0.02%) and vitamin C (0.1~1%) were mixed, to which purified water (79~94%) was added to make syrup. The prepared syrup was sterilized at 85~98° C. for 20~180 seconds, then mixed with cooling water at the ratio of 1:4. Then, carbon dioxide gas (0.5~0.82%) was given to the mixture to prepare carbonated beverages containing the herbal mixture extract of the present invention.

<3-2> Preparation of Health Beverages

Acid fructose (0.5%), oligosaccharide (2%), sugar (2%), salt (0.5%) and water (75%) were all mixed with the herbal mixture extract evenly, followed by sterilization. The mixture was put in a small container such as a glass bottle or pat bottle, resulting in health beverages.

<3-3> Preparation of Vegetable Juice 5 g of the herbal mixture extract of the present invention was added to 1,000 ml of tomato or carrot juice to prepare health vegetable juice.

<3-4> Preparation of Fruit Juice 1 g of the herbal mixture extract of the present invention was added to 1,000 ml of apple or grape juice to produce health fruit juice.

INDUSTRIAL APPLICABILITY

As explained hereinbefore, the herbal mixture extract of *Notoginseng radix, Rehmanniae radix preparata* and *Acanthopanacis cortex* of the present invention has excellent activities of inhibiting the release of an inflammatory substance, which is one of the critic causes of arthritis, and suppressing the synthesis of a matrix destroying substance (MMP-13), which is a cartilage destroying factor, compared with an individual extract of each. Moreover, inhibition of the progress of arthritis in animal models was greater when the herbal mixture extract of the present invention was administered than when single extract of each was administered respectively. Therefore, the herbal mixture extract of *Notoginseng radix, Rehmanniae radix preparata* and *Acanthopanacis cortex* can be effectively used not only for the prevention and the treatment of arthritis but also for improving health condition.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An extract of an herbal mixture of *Notoginseng radix, Rehmanniae radix preparata* and *Acanthopanacis cortex* for treating arthritis in a mammal, wherein the ratio by weight of *Notoginseng radix:Rehmanniae radix preparata:Acanthopanacis cortex* is 30 to 70:20 to 60:0.5 to 20.

2. The extract according to claim 1, wherein the ratio by weight of *Notoginseng radix:Rehmanniae radix preparata: Acanthopanacis cortex* is 40 to 60:30 to 50:5 to 15.

3. The extract according to claim 1, wherein the ratio by weight of *Notoginseng radix:Rehmanniae radix preparata: Acanthopanacis cortex* is 50:40:10.

4. The extract according to claim 1, wherein the extract is prepared by extracting the herbal mixture with water, $C_1$~$C_4$ alcohol or mixture thereof.

5. The extract according to claim 1, wherein the arthritis is rheumatoid arthritis.

6. The extract according to claim 1, wherein the arthritis is degenerative arthritis.

7. The extract according to claim 1, wherein the extract inhibits the release of tumor necrosis factor α (TNF-α) in the mammal.

8. The extract according to claim 1, wherein the extract inhibits the generation of nitric oxide (NO) in the mammal.

9. The extract according to claim 1, wherein the extract inhibits the synthesis of matrix metalloproteinase-13 (MMP-13).

10. A health food comprising the extract of claim 1 as an effective ingredient.

11. A pharmaceutical composition for treating arthritis comprising the extract of claim 1 as an effective ingredient.

12. A method for treating arthritis in a mammal in need thereof comprising administering a pharmaceutically effective amount of the extract of claim 1 to the mammal.

13. The method according to claim 12, wherein the arthritis comprises rheumatoid arthritis.

14. The method according to claim 13, wherein the arthritis comprises degenerative arthritis.

15. A method for inhibiting the progress of arthritis in a mammal in need thereof comprising administering a pharmaceutically effective amount of the extract of claim 1 to the mammal.

* * * * *